(12) United States Patent
Wittenberger et al.

(10) Patent No.: US 8,679,105 B2
(45) Date of Patent: Mar. 25, 2014

(54) DEVICE AND METHOD FOR PULMONARY VEIN ISOLATION

(75) Inventors: Dan Wittenberger, L'ile Bizard (CA); Ioana Alina Deac, Vaudreuil-Dorion (CA); Jean-Pierre Lalonde, Candiac (CA); Deborah A. De Roy, Dollard-des-Ormeaux (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 816 days.

(21) Appl. No.: 12/845,312

(22) Filed: Jul. 28, 2010

(65) Prior Publication Data

US 2012/0029494 A1    Feb. 2, 2012

(51) Int. Cl.
*A61B 18/02* (2006.01)

(52) U.S. Cl.
USPC .............................................. 606/21; 606/41

(58) Field of Classification Search
USPC .............. 606/21–28, 41, 42, 45–50; 607/101, 607/102, 116
See application file for complete search history.

(56) References Cited

U.S. PATENT DOCUMENTS

| | | | |
|---|---|---|---|
| 6,325,797 B1 * | 12/2001 | Stewart et al. | 606/41 |
| 6,368,304 B1 * | 4/2002 | Aliberto et al. | 604/113 |
| 6,491,710 B2 | 12/2002 | Satake | |
| 6,529,756 B1 * | 3/2003 | Phan et al. | 600/374 |
| 6,537,271 B1 * | 3/2003 | Murray et al. | 606/21 |
| 6,602,276 B2 * | 8/2003 | Dobak et al. | 607/105 |
| 6,620,131 B2 * | 9/2003 | Pham et al. | 604/113 |
| 6,645,199 B1 * | 11/2003 | Jenkins et al. | 606/41 |
| 6,652,517 B1 * | 11/2003 | Hall et al. | 606/41 |
| 6,702,811 B2 * | 3/2004 | Stewart et al. | 606/41 |
| 6,814,733 B2 | 11/2004 | Schwartz et al. | |
| 6,866,662 B2 * | 3/2005 | Fuimaono et al. | 606/41 |
| 7,089,063 B2 | 8/2006 | Lesh et al. | |
| 7,137,395 B2 | 11/2006 | Fried et al. | |
| 7,192,438 B2 | 3/2007 | Margolis | |
| 7,195,628 B2 | 3/2007 | Falkenberg | |
| 7,285,119 B2 | 10/2007 | Stewart et al. | |
| 7,340,307 B2 | 3/2008 | Maguire et al. | |
| 7,367,970 B2 | 5/2008 | Govari et al. | |
| 7,435,248 B2 | 10/2008 | Taimisto et al. | |
| 7,655,005 B2 * | 2/2010 | Bhola | 606/41 |

FOREIGN PATENT DOCUMENTS

| | | |
|---|---|---|
| CA | 2666334 A1 | 3/2003 |
| CA | 2673180 A1 | 4/2008 |

* cited by examiner

*Primary Examiner* — Michael Peffley
(74) *Attorney, Agent, or Firm* — Christopher & Weisberg, P.A.

(57) ABSTRACT

An intravascular catheter is provided, including a flexible elongate body; an expandable element positioned on the elongate body; a substantially linear thermal segment located distally of the expandable element; a first fluid flow path in fluid communication with the expandable element; and a second fluid flow path in fluid communication with the substantially linear thermal segment.

8 Claims, 4 Drawing Sheets

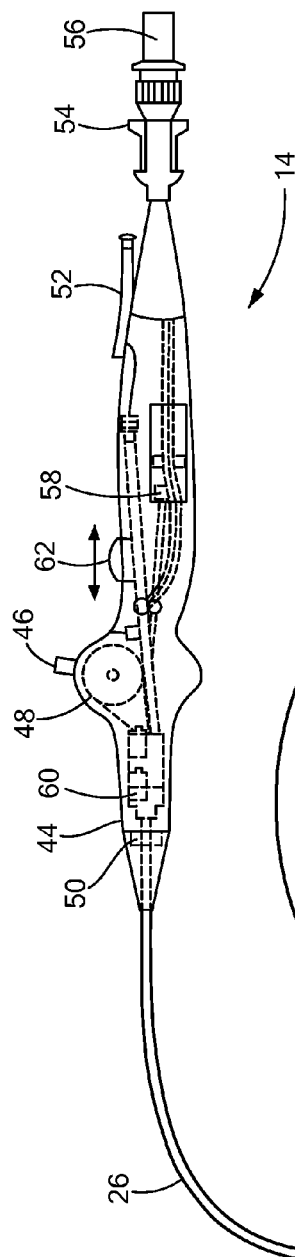
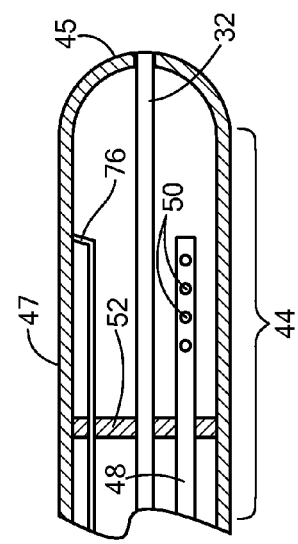
FIG. 2
FIG. 3

DEVICE AND METHOD FOR PULMONARY VEIN ISOLATION

CROSS-REFERENCE TO RELATED APPLICATION n/a

STATEMENT REGARDING FEDERALLY SPONSORED RESEARCH OR DEVELOPMENT n/a

FIELD OF THE INVENTION

The present invention relates to a method and system for tissue treatment, and in particular, towards systems and methods of use thereof for thermally ablating cardiac tissue.

BACKGROUND OF THE INVENTION

Minimally invasive devices, such as catheters, are often employed for surgical procedure, including those involving ablation, dilation, and the like. In a particular situation, an ablation procedure may involve creating a series of interconnecting or otherwise continuous lesions in order to electrically isolate tissue believed to be the source of an arrhythmia. During the course of such a procedure, a physician may employ several different catheters having variations in the geometry and/or dimensions of the ablative element in order to produce the desired ablation pattern and/or continuity. Each catheter may have a unique geometry for creating a specific lesion or pattern, with the multiple catheters being sequentially removed and replaced during a designated procedure to create the desired multiple lesions constituting a pattern or continuous segment of treated tissue. Exchanging these various catheters during a procedure can cause inaccuracies or movement in the placement and location of the distal tip with respect to the tissue to be ablated, and may further add to the time required to perform the desired treatment. These potential inaccuracies and extended duration of the particular procedure, not to mention the risks of complications from repeatedly inserting and retracting devices to and from an incision site, increase the risk to the patient undergoing treatment. Accordingly, it would be desirable to provide a single medical device having the ability to provide ablative patterns of various shapes and continuity, without the need for additional catheters or the like having a single geometric orientation, and thus, limited in the ability to provide multiple ablative patterns or treatment continuity for a specific tissue region.

SUMMARY OF THE INVENTION

The present invention advantageously provides a method and system having the ability to provide treatment to regions of varying shapes and continuity. In particular, a medical device is provided having an elongate catheter body; a first thermal treatment region on the catheter body; a second thermal treatment region distal to the first treatment region, where the second thermal treatment region is operable independently from the first thermal treatment region. The first thermal treatment region may include an expandable element and the second treatment region may include a substantially linear thermal segment, an elongated metallic surface, and/or may be deflectable independently from the first treatment region. The length of the second thermal treatment region may be controllably and/or selectively adjustable. The device may include a first fluid flow path in fluid communication with the first thermal treatment region, a second fluid flow path in fluid communication with the second thermal treatment region, and a cryogenic fluid source in fluid communication with at least one of the first and second fluid flow paths.

An intravascular catheter is also provided, including an elongate body; an expandable element positioned on the elongate body; an elongated thermal segment located distally of the expandable element; a first fluid flow path in fluid communication with the expandable element; and a second fluid flow path in fluid communication with the elongated thermal segment, where the first fluid flow path may be operable independently from the second fluid flow path. The first fluid flow path may include a first fluid injection lumen, and the second fluid flow path may include a second fluid injection lumen, while the first fluid flow path and the second fluid flow path may include a common exhaust lumen.

A method of treating cardiac tissue is also provided, including, positioning an expandable element of a medical device proximate a pulmonary vein; ablating tissue proximate the pulmonary vein with the expandable element; positioning an elongate thermal segment of the medical device proximate the pulmonary vein; and ablating tissue proximate the pulmonary vein with the elongate thermal segment. Ablating tissue with the expandable element may include creating a substantially arcuate lesion, and ablating tissue with the elongate thermal segment may include creating a lesion substantially continuous with the arcuate lesion. The method may include deflecting the thermal segment independently of the expandable element, and positioning the expandable element may include expanding the expandable element to substantially occlude at least a portion of the pulmonary vein. The method may also include collapsing the expandable element prior to positioning the elongate thermal segment and ablating tissue may include the delivery a cryogenic fluid into either and/or both of the expandable element and thermal segment.

BRIEF DESCRIPTION OF THE DRAWINGS

A more complete understanding of the present invention, and the attendant advantages and features thereof, will be more readily understood by reference to the following detailed description when considered in conjunction with the accompanying drawings wherein:

FIG. 2 is an illustration of an embodiment of a medical device constructed in accordance with the principles of the present invention;

FIG. 3 is an additional illustration of the medical device shown in FIG. 2;

DETAILED DESCRIPTION OF THE INVENTION

Figure 1:
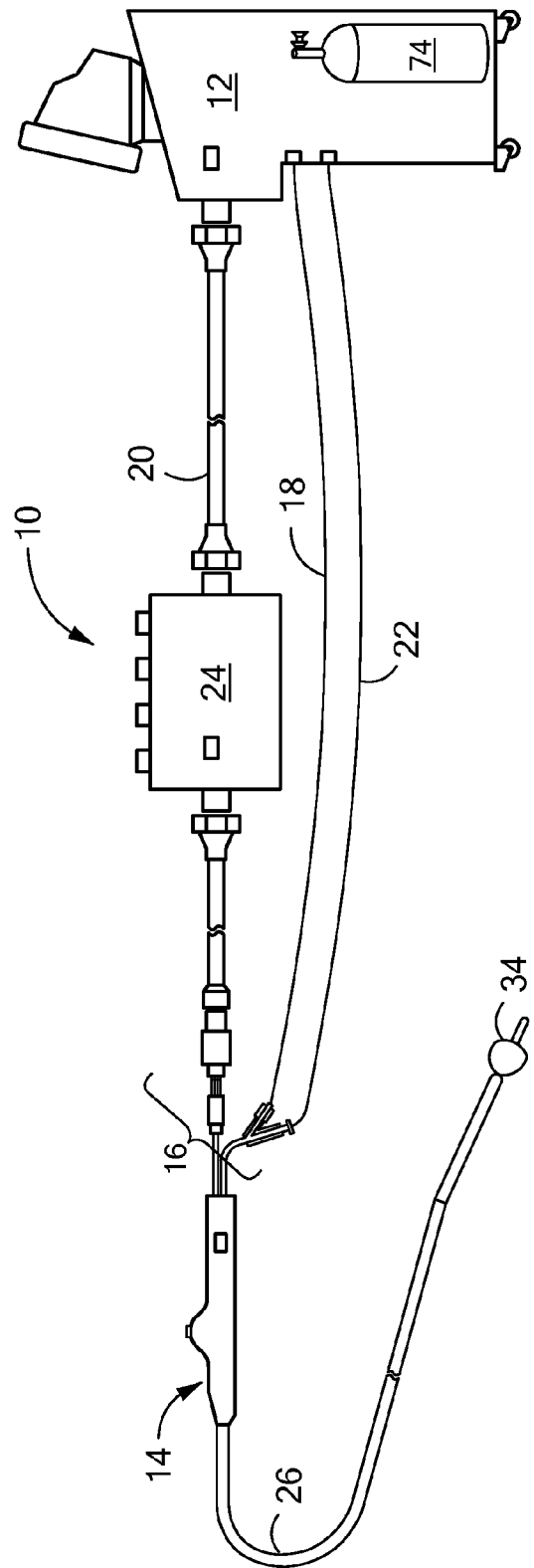
FIG. 1 is an illustration of an embodiment of a medical system constructed in accordance with the principles of the present invention.

The present invention advantageously provides a medical system having the ability to provide variously-shaped lesions or ablation segments at a designated tissue sites, and further providing an ability to ensure continuity of an ablation lesion or pattern. Referring now to the drawing figures in which like reference designations refer to like elements, an embodiment of a medical system constructed in accordance with principles of the present invention is shown in FIG. 1 and generally designated as "10." The system generally includes a control unit or console 12 coupled to a medical device 14 through an umbilical system 16. The medical device 14 may be a medical probe, a catheter, a balloon-catheter, as well as other devices deliverable or otherwise positionable through the vasculature and/or proximate to a tissue region for treatment. In particular, the medical device 14 may include a device operable to thermally treat a selected tissue site, including cardiac tissue. The medical system 10 may also include one or more sensors to monitor the operating parameters throughout the system, including for example, pressure, temperature, flow rates, volume, or the like in the console 12, the umbilical system 16, and/or the medical device 14.

Umbilical system 16 may include three separate umbilicals: a coaxial umbilical 18, an electrical umbilical 20 and a vacuum umbilical 22. Although separate umbilicals are shown, it is contemplated that one or more connections may be included in one or more umbilicals having one or more coaxial or otherwise integrally contained passages or conduits therethrough providing electrical and fluid communication between the medical device 14 and the console 12. An outer vacuum umbilical may be suitable for a medical device having multiple layers or balloons. If the user wishes to perform a radiofrequency ("RF") ablation procedure, radiofrequency energy can be provided to electrodes on the medical device 14 via electrical umbilical 20 to perform an RF ablation technique. Electrical umbilical 20 can include an electrocardiograph ("ECG") box 24 to facilitate a connection from one or more electrodes on the medical device 14 to an ECG monitor (not shown). Coaxial umbilical 18 may include both a cooling injection umbilical and a vacuum umbilical that provide respective inlet and return paths for a refrigerant or coolant used to cool a tissue-treating section of the device 14. The vacuum umbilical 22 may provide a safety conduit allowing excess coolant or gas to escape from the device 14 if the pressure within the medical device 14 exceeds a predefined limit. The vacuum umbilical 22 can also be used to capture and remove air or blood leaking into the outer vacuum system when portions of the device are outside or inside the patient, respectively.

Now referring to FIG. 2, the medical device 14 is shown in more detail. The medical device 10 may include an elongate body 26 passable through a patient's vasculature. The elongate body 26 may define a proximal portion and a distal portion, and may further include one or more lumens disposed within the elongate body 26 thereby providing mechanical, electrical, and/or fluid communication between the proximal portion of the elongate body 26 and the distal portion of the elongate body 26. For example, the elongate body 26 may include an injection lumen 28 and an exhaust lumen 30 defining a fluid flow path therethrough. In addition, the elongate body 26 may include a guidewire lumen 32 movably disposed within and/or extending along at least a portion of the length of the elongate body 26 for over-the-wire applications. The guidewire lumen 32 may define a proximal end and a distal end, and the guidewire lumen 32 may be movably disposed within the elongate body 26 such that the distal end of the guidewire lumen 32 extends beyond and out of the distal portion of the elongate body 26.

The medical device may include one or more treatment regions for energetic or other therapeutic interaction between the medical device 14 and a treatment site. The treatment regions may deliver, for example, radiofrequency energy, cryogenic therapy, or the like to a tissue area in proximity to the treatment region(s). For example, the device 14 may include a first treatment region 34 having a thermal treatment element, such as an expandable membrane or balloon and/or one or more electrodes or other thermally-transmissive components, at least partially disposed on the elongate catheter body. In a particular example, the first treatment region 34 may include a first expandable/inflatable element or balloon 36 defining a proximal end coupled to the distal portion of the elongate body 26 of the medical device 14, while further defining a distal end coupled to the distal end of the guidewire lumen 32. As such, due to the movable nature of the guidewire lumen 32 about the elongate body 26, any axial and/or longitudinal movement of the guidewire lumen 32 may act to tension or loosen the first expandable element 36, i.e., extend or retract the expandable element 36 from a lengthened state to a shortened state during an inflation or deflation thereof. In addition, the first expandable element 36 may have any of a myriad of shapes, and may further include one or more material layers providing for puncture resistance, radiopacity, or the like. The first expandable element 36 may be in communication with the fluid injection and exhaust lumens of the medical device 14 as described above. In addition, the fluid injection and/or exhaust lumens may be slidably positionable and movable within the expandable element 36 to direct coolant or fluid dispersion towards a desired portion of the expandable element 36, such as distal or proximal portion.

The medical device 14 may further include a second expandable/inflatable element or balloon 38 contained within or otherwise encompassed by the first expandable element 36 such that an interstitial region, envelope or space 40 is defined therebetween. The second expandable element 38 may be in communication with the fluid injection and exhaust lumens of the medical device 14 as described above, i.e., a first fluid flow path may provide an inflation fluid or coolant, such as a cryogenic fluid or the like, to the interior of the second expandable element 38. Further, the interstitial region 40 may be in fluid communication with an interstitial lumen 42 providing a second fluid flow path or avenue separate and independent from a fluid flow path delivering fluid or otherwise in communication with an interior of the second expandable element 38. The second pathway provides an alternate exhaust route for fluid that may leak from the interior of the second expandable element 38 into the interstitial region 40 or fluid entering the medical device 14 from the exterior. In particular, the isolation of the interstitial lumen 42 from the interior of the second expandable element 38 provides an alternate route for fluid to circulate in the case of a rupture or leak of either the first or second expandable elements, as well as allowing for the injection or circulation of fluids within the interstitial region 40 independently of fluids directed towards the second expandable element 38. Towards that end, the interstitial region may be in fluid communication with a fluid source, a vacuum source, or the like separate from a fluid source, vacuum source or otherwise in fluid communication with the interior of the second expandable element 38. Alternatively, the interstitial lumen 42 may be joined to or otherwise in fluid communication with the injection lumen 28 and the interior of the second expandable element 38 to provide a single exhaust or vacuum source for the medical device 14.

While the first treatment region 34 may be in fluid communication with a cryogenic fluid source to cryogenically treat selected tissue, it is also contemplated that the first treatment region alternatively includes one or more expandable elements or balloons having electrically conductive portions or electrodes thereon coupled to a radiofrequency generator or power source as the treatment modality.

As shown in FIGS. 2-3, the medical device may further include a second treatment region 44 located distally of the first treatment region 34. The second treatment region 44 may include an elongated thermal treatment segment or element providing for "spot" ablation of discrete tissue locations using its distal tip or face 45, while also providing the capacity to deliver therapeutic treatment in an elongated, substantially linear form using its lateral or exterior surfaces 47. The longitudinal length of the second treatment region 44 may also be adjustable. For example, the second treatment region 44 may include a stretchable, corrugated or bellows-shaped configuration that can be transitioned from a first length to a second increased length. The transition may be achieved through the application of an increased pressure within the second treatment region 44 to cause the desired lengthening, and may also be achieved by manipulation of one or more mechanical assemblies operable at the handle. The second treatment region 44 may further provide for anchoring of the distal end of the medical device 14 through cryoadhesion with contacted tissue when either of the first or second treatment regions 34, 44 are in use.

The second treatment region 44 may be constructed from one or more materials imparting thermally conductive properties, including metals, thermally conductive polymers, and/or composites thereof such as nylon, polyethylene terephthalate ("PET"), and/or polyethylene ("PE") for example. In particular, the second treatment region 44 may provide sufficient thermal conductivity for ablation of contacted tissue through the use of a cryogenic refrigerant or a radiofrequency or other thermal energy source coupled to or otherwise in thermal communication with the thermal segment. Such thermal communication may be achieved, for example, by a fluid flow path in fluid communication with the second treatment region 44 that is independently operated or otherwise at least partially separated from a fluid flow path delivering a cooling or treatment medium to the first treatment region 34. The second treatment region 44 may thus be operable independently and separately from the first treatment region 34. In particular, the second treatment region 44 may be fluidically isolated or sealed from fluid flow with the first treatment region 34. For example, a secondary fluid injection lumen 48 may be in fluid communication with an interior of the second treatment region 44. The secondary fluid injection lumen 48 may include one or more apertures 50 therein for dispersing, expanding, or otherwise delivering a fluid to the second treatment region 44. The secondary fluid injection lumen 48 may be placed in fluid communication with a fluid supply common to the first treatment region 34, or may be coupled to a separate and independently operated fluid source. Where a common fluid source is elected, one or more valves, controllers, or the like may provide for the controlled, independent, and/or separate dispersion or circulation of fluid through the two injection lumens/fluid paths. Such valves, controllers, or the like may be located in a portion of the medical device 14 and/or in the console 12.

The second treatment region 44 may further include a sealed transverse section or wall 52 spanning from an outer wall, layer or circumference of the elongate body 26 and around the one or more lumens extending towards the distal portion of the medical device that reduce or wholly prevent fluid dispersed within the first treatment region 34 from travelling distally towards the second treatment region 44, and vice versa. The second treatment region 44 may further include a secondary exhaust lumen (not shown), or the exhaust lumen 30 may be in fluid communication with both the first and second treatment regions 34, 44 thereby allowing a single exhaust or vacuum source to remove expended coolant from both the first and second treatment regions jointly. Where the exhaust lumen 30 is in fluid communication with both of the treatment regions, the pressure gradient resulting from the exhaust or vacuum source may be selected to substantially reduce distal movement of fluid injected into the first treatment region, and may further be sufficient to facilitate removal of fluid injected into the second treatment region 44 while avoiding inflation of a balloon or expandable element of the first treatment region 34. Control and operation of the vacuum source or pressure gradient of the exhaust lumen 30 can thus aid in independently operating the thermal delivery of the first and second treatment regions even if the first and second treatment regions are in substantial fluid communication with each other.

The first and second treatment regions 34, 44 may generally provide the ability to deliver therapeutic treatment to in a variety of different geometric configurations, dimensions or shapes with a single device. In addition, the first and second treatment regions 34, 44 may provide varying degrees of precision in treating tissue and/or creating an ablative lesion as a result of their respective geometric configurations, shapes, and/or dimensions. For example, the first treatment region 34 may be used during an initial stage of a procedure to treat a relatively large area of tissue, while the second treatment region 44 may subsequently be used to treat smaller sections or specific areas of tissues within the broad region that require additional therapy. In a particular example, as described above, the first treatment region 34 may include one or more expandable elements or balloons. The first treatment region 34 may thus provide for arcuate, circular, and/or circumferential treatment patterns. In turn, the second treatment region 44 may include an elongate, substantially linear thermal segment enabling energetic or thermal exchange with a contacted tissue area with either its tip 45 for "spot" lesion formation or lateral surfaces 47 for elongated lesion formation. The second treatment 44 region may allow a physician to "fill in" or otherwise treat discrete areas in proximity to the initial area treated by the first treatment region 34 to ensure continuity of the treated tissue, such as a continuous ablation lesion or electrical conduction block for example. Of note, the second treatment region 44 may be substantially linear when not experiencing any external loading or force, but may retain sufficient flexibility to curve or deflect into an arcuate, curvilinear shape via one or more steering or deflection mechanisms facilitating contact with a desired tissue region.

The medical device 14 may further include one or more temperature and/or pressure sensors (not shown) proximate the treatment region(s) for monitoring, recording or otherwise conveying measurements of conditions within the medical device 14 or the ambient environment at the distal portion of the medical device 14. The sensor(s) may be in communication with the console 12 for initiating or triggering one or more alerts or therapeutic delivery modifications during operation of the medical device 14.

Referring again to FIG. 2, the medical device 14 may include a handle 54 coupled to the proximal portion of the elongate body 26, where the handle 54 may include an element such as a lever or knob 56 for manipulating the catheter body and/or additional components of the medical device 14. For example, a pull wire 58 with a proximal end and a distal end may have its distal end anchored to the elongate body 26 at or near the distal end. The proximal end of the pull wire 58 may be anchored to an element such as a cam in communication with and responsive to the lever 56.

The handle 54 can further include circuitry for identification and/or use in controlling of the medical device 14 or another component of the system. For example, the handle may include one or more pressure sensors 60 to monitor the fluid pressure within the medical device 14. Additionally, the handle may be provided with a fitting 62 for receiving a guidewire that may be passed into the guidewire lumen 32.

The handle 54 may also include connectors that are matable directly to a fluid supply/exhaust and control unit or indirectly by way of one or more umbilicals. For example, the handle may be provided with a first connector 64 that is matable with the co-axial fluid umbilical 18 and a second connector 66 that is matable with the electrical umbilical 20. The handle 54 may further include blood detection circuitry 68 in fluid and/or optical communication with the injection, exhaust and/or interstitial lumens. The handle 54 may also include a pressure relief valve 70 in fluid communication with the injection, exhaust and/or interstitial lumens to automatically open under a predetermined threshold value in the event that value is exceeded.

Continuing to refer to FIG. 2, the medical device 14 may include an actuator element 72 that is movably coupled to the proximal portion of the elongate body 26 and/or the handle 54. The actuator element 72 may further be coupled to the proximal portion of the guidewire lumen 32 such that manipulating the actuator element 72 in a longitudinal direction causes the guidewire lumen 32 to slide towards either of the proximal or distal portions of the elongate body 26. As a portion of either and/or both the first and second expandable elements 36,38 may be coupled to the guidewire lumen 32, manipulation of the actuator element 72 may further cause the expandable element(s) to be tensioned or loosened, depending on the direction of movement of the actuator element 72, and thus, the guidewire lumen 32. Accordingly, the actuator element 72 may be used to provide tension on the expandable element(s) 36,38 during a particular duration of use of the medical device 14, such as during a deflation sequence, for example. The actuator element 72 may include a thumb-slide, a push-button, a rotating lever, or other mechanical structure for providing a movable coupling to the elongate body 26, the handle 54, and/or the guidewire lumen 32. Moreover, the actuator element 72 may be movably coupled to the handle 54 such that the actuator element 72 is movable into individual, distinct positions, and is able to be releasably secured in any one of the distinct positions.

Referring again to FIG. 3, the second treatment region 44 may be deflectable, steerable, or otherwise manipulated into a desired position or configuration independently or differently from the first treatment region 34 and/or adjacent portions of the elongate body 26. In particular, the elongate body 26 of the medical device 14 may be constructed from one or more layers of material or differing components to provide a desired degree of flexibility while maintaining the capability to transmit torque along the length of the medical device 14. The layers may include a multitude of polymers, plastics, and composites thereof, as well as braided or other structural reinforcing materials/components running therethrough that substantially dictate its resulting deflection or bending behavior when a force is applied, i.e., its deflection profile. The elongate body 26 may further include one or more steering wires 76 or actuation mechanisms to deliver a force to a particular segment or portion of the medical device 14, such as the second treatment region 44, in addition to the pull wire 58 described above, which may provide deflection or steering of the first treatment region 34. The steering wire 76 may be attached to or otherwise coupled to a secondary steering actuator (not shown) such as a knob, lever, or the like, that is independently operable of the lever 56.

In an exemplary system, a fluid supply 80 including a coolant, cryogenic refrigerant, or the like, an exhaust or scavenging system (not shown) for recovering or venting expended fluid for re-use or disposal, as well as various control mechanisms for the medical system may be housed in the console 12. In addition to providing an exhaust function for the catheter fluid supply, the console 12 may also include pumps, valves, controllers or the like to recover and/or re-circulate fluid delivered to the handle 54, the elongate body 26, and treatment region(s) 34,44 of the medical device 14. A vacuum pump in the console 12 may create a low-pressure environment in one or more conduits within the medical device 14 so that fluid is drawn into the conduit(s) of the elongate body 26, away from the treatment region(s) 34, 44, and towards the proximal end of the elongate body 26. The console 12 may include one or more controllers, processors, and/or software modules containing instructions or algorithms to provide for the automated operation and performance of the features, sequences, or procedures described herein.

Figure 4:
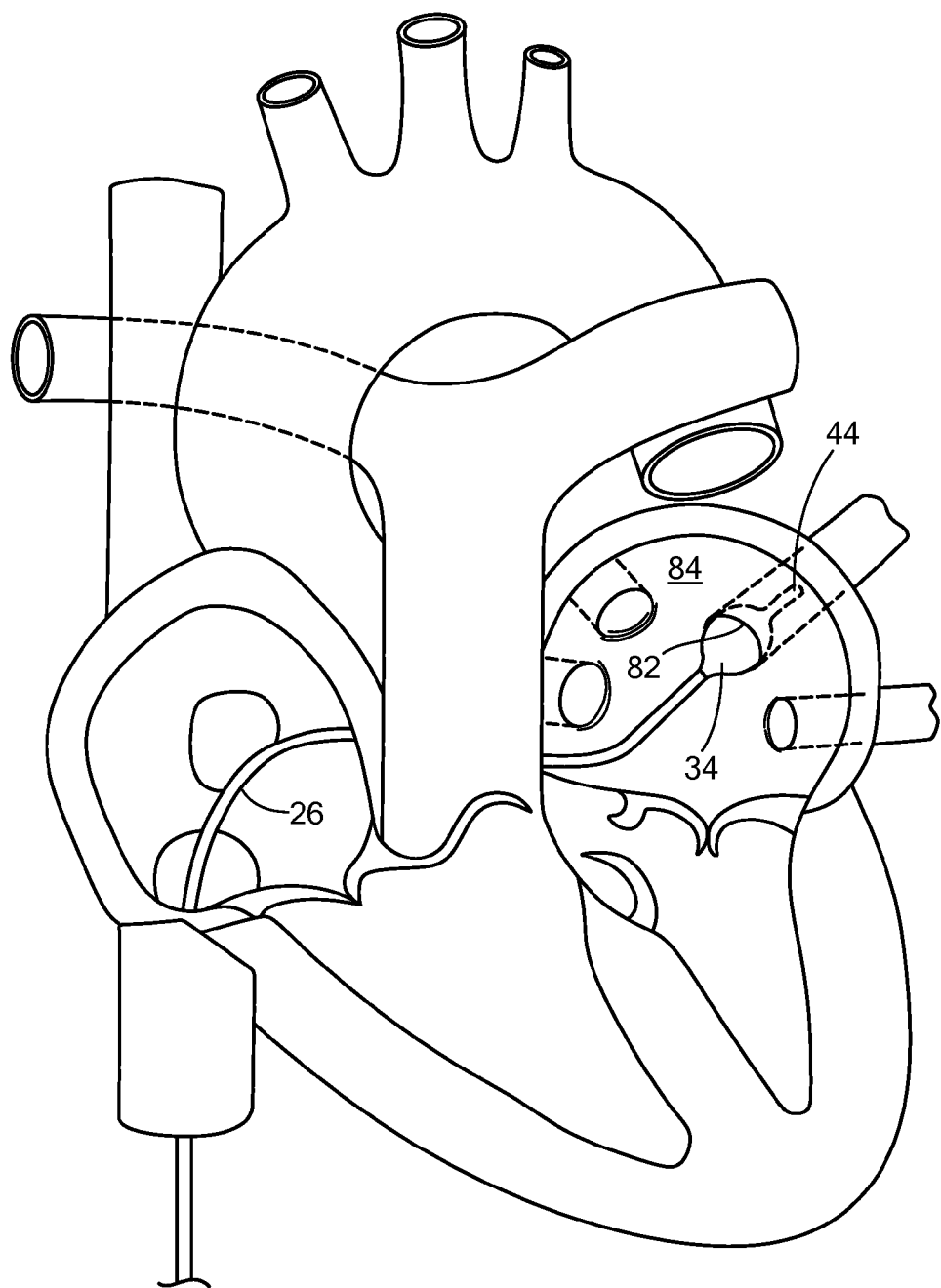
FIG. 4 is an illustration of an exemplary use of the medical system and device shown in FIGS. 1 and 2.
Figure 5:
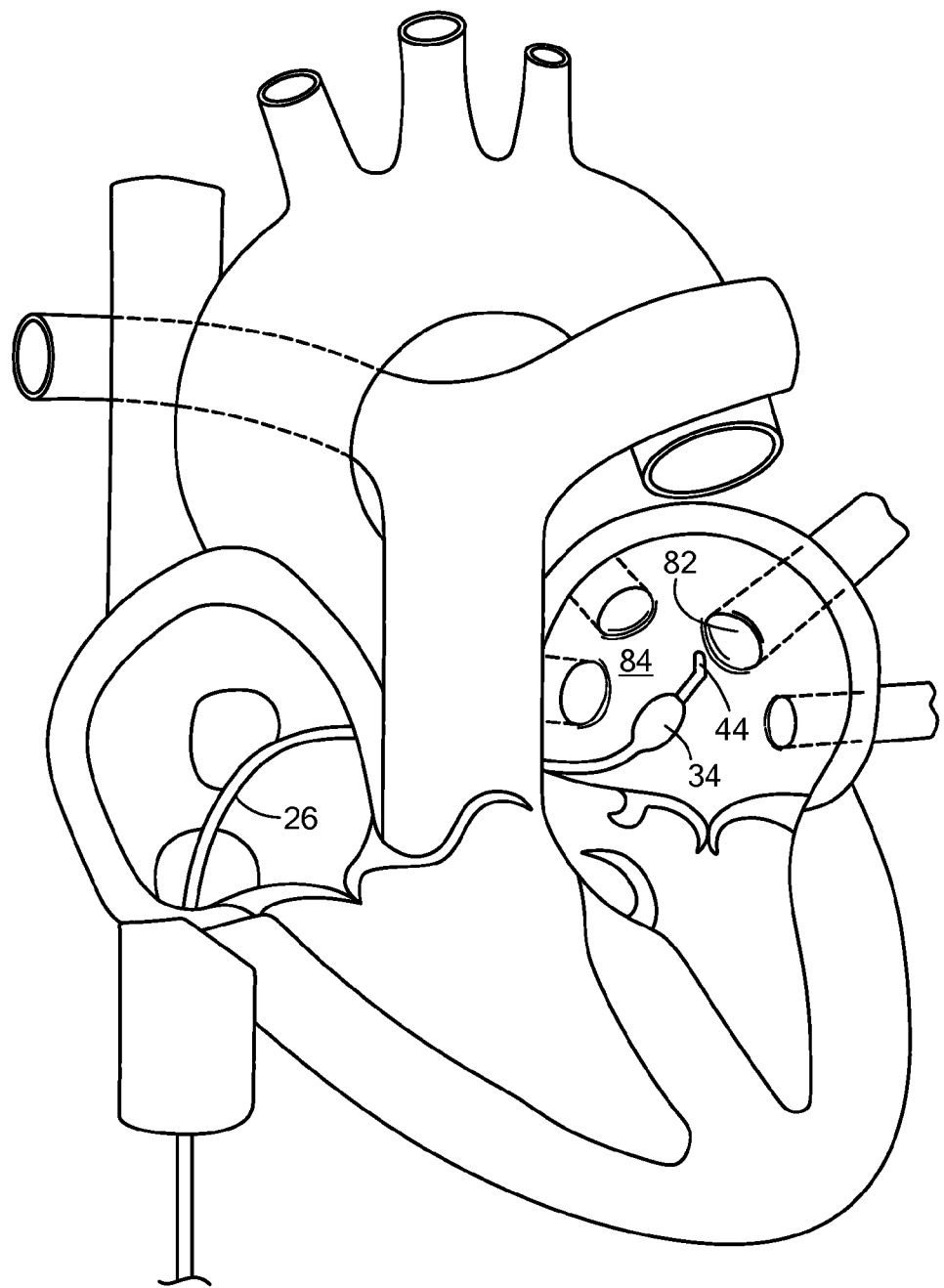
FIG. 5 is an additional illustration of an exemplary use of the medical system and device shown in FIGS. 1 and 2.

Now referring to FIGS. 4-5, in an exemplary method of use, the medical system 10 may be used to deliver therapeutic treatment to a targeted tissue area. For example, the medical device 14 may be positioned and operated to thermally treat or ablate a targeted tissue region in the heart. The first treatment region 34 may be positioned in the proximity of an opening or orifice in the targeted tissue area, such as a pulmonary vein opening or junction 82 with a portion of the atrial wall 84, for example. Where the first treatment region 34 includes an expandable element, the expandable element may be inflated or otherwise expanded to substantially occlude the pulmonary vein. The occlusion reduces the blood flow around the treatment region 34, thereby allowing enhanced thermal exchange between the medical device 14 and the targeted tissue. The occlusion may further anchor a distal portion of the medical device 14, thereby facilitating additional maneuvering, deflection, or the like of proximal portions of the catheter body 26.

Once the first treatment region 34 has been positioned where desired, it may be operated to thermally treat the tissue. For example, a cryogenic coolant or fluid may be circulated through the first treatment region 34, thereby reducing the temperature of the first treatment element and the tissue in proximity to it. The extent of the thermal exchange and/or realized temperatures of the treatment area and thus the tissue may be manipulated by one or more controls in the console 12 to provide for tissue ablation, mapping, or otherwise.

Upon completion of a treatment cycle or selected duration with the first treatment region 34, the medical device 14 may be repositioned such that the second treatment region 44 is in proximity to the tissue region previously treated by the first treatment region 34. For example, where the first treatment region 34 includes an inflatable element, the initially treated tissue region may include a substantially arcuate or circular area. The second treatment region 44, through deflection or other maneuvering, may be positioned in proximity to the arcuate or circular area. The length of the second treatment 44 may be adjusted through the manipulation of a pressure level within the treatment element and/or by the use of a mechanical control mechanism or assembly, such as a steering wire or the like, to attain the desired length of the treatment region 44 for treating a particularly dimensioned region or area of the tissue. Subsequently, the second treatment region 44 may be operated to thermally treat tissue adjacent to or otherwise continuous with the tissue initially targeted with the first treatment element 34. The difference in geometric profiles between the first and second treatment regions 34, 44 allows the second treatment region 44 to deliver therapeutic thermal energy to specific tissue areas having smaller dimensions or otherwise requiring more precision than is available with the first treatment region 34. The second treatment region 44 can thus be used to "touch up" or ensure the desired area is completely treated. For example, the desired treatment may include substantially surrounding or circumscribing a region of tissue, such as the pulmonary vein, with an ablative lesion or conduction block. The first treatment region 34 can be used to create a substantially arcuate or circular lesion, while the second treatment 44 region can be used to treat discontinuities or specific spots on the arcuate lesion pattern (or in the vicinity thereof). The second treatment region 44 may also be used to create additional spot, linear or arcuate treatment areas.

The first treatment region 34 may also be used to aid in positioning and/or insulating at least a portion of the second treatment region 44 during use. For example, the second treatment region 44 may be steered or deflected to contact a tissue area. The first treatment region 34 may then be manipulated to contact a portion of the second treatment region 44, thereby applying pressure to the second treatment region to increase its contact with the targeted tissue area. Further, by surrounding or contacting a portion of the second treatment region 44 with the first treatment region 34, the second treatment region will be insulated from the surrounding environment, i.e, blood flow or the like, and thus have increased thermal conductivity and efficiency in treating the contacted tissue.

Accordingly, the medical system described above provides variously-shaped lesions or ablation segments at a designated tissue sites, and further provides an ability to ensure continuity of an ablation lesion or pattern with a single device, rather than with several different devices.

It will be appreciated by persons skilled in the art that the present invention is not limited to what has been particularly shown and described herein above. In addition, unless mention was made above to the contrary, it should be noted that all of the accompanying drawings are not to scale. A variety of modifications and variations are possible in light of the above teachings without departing from the scope and spirit of the invention, which is limited only by the following claims.

What is claimed is:

1. A medical device, comprising:
   an elongate catheter body;
   a first thermal treatment region on the catheter body;
   a substantially linear second thermal treatment region distal to the first treatment region, wherein the second thermal treatment region includes an elongated metallic surface and is operable independently from the first thermal treatment region;
   a first fluid flow path in fluid communication with the first thermal treatment region; and
   a second fluid flow path at least partially disposed within and in fluid communication with the substantially linear second thermal treatment region.

2. The medical device of claim 1, wherein the first thermal treatment region includes an expandable element.

3. The medical device of claim 1, wherein the second thermal treatment region is deflectable independently from the first treatment region.

4. The medical device of claim 1 further comprising a cryogenic fluid source in fluid communication with at least one of the first and second fluid flow paths.

5. The intravascular catheter of claim 1, wherein the first fluid flow path is operable independently from the second fluid flow path.

6. The intravascular catheter of claim 1, wherein the first fluid flow path includes a first fluid injection lumen, and the second fluid flow path includes a second fluid injection lumen.

7. The intravascular catheter of claim 1, wherein the first fluid flow path and the second fluid flow path include a common exhaust lumen.

8. A medical device, comprising:
   an elongate catheter body;
   a first thermal treatment region on the catheter body;
   a substantially linear second thermal treatment region distal to the first treatment region, wherein the second thermal treatment region is operable independently from the first thermal treatment region and the length of the second thermal treatment region is adjustable;
   a first fluid flow path in fluid communication with the first thermal treatment region; and
   a second fluid flow path at least partially disposed within and in fluid communication with the substantially linear second thermal treatment region.

* * * * *